United States Patent
Awadi et al.

(10) Patent No.: US 10,690,104 B1
(45) Date of Patent: Jun. 23, 2020

(54) METHOD AND SYSTEM FOR ENGINE START/STOP CONTROL

(71) Applicant: Ford Global Technologies, LLC, Dearborn, MI (US)

(72) Inventors: Ahmed Awadi, Farmington Hills, MI (US); Hussam Makkiya, Dearborn, MI (US); Hafiz Khafagy, Dearborn, MI (US); Abraham Mezaael, Southfield, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 16/243,891

(22) Filed: Jan. 9, 2019

(51) Int. Cl.
| F02N 11/08 | (2006.01) |
| B60H 3/00 | (2006.01) |
| A61L 9/01 | (2006.01) |
| B60H 1/32 | (2006.01) |

(52) U.S. Cl.
CPC .............. *F02N 11/084* (2013.01); *A61L 9/01* (2013.01); *B60H 3/0021* (2013.01); *B60H 3/0035* (2013.01); *F02N 11/0822* (2013.01); *A61L 2209/11* (2013.01); *A61L 2209/16* (2013.01); *B60H 1/3222* (2013.01)

(58) Field of Classification Search
CPC ...... F02N 11/084; F02N 11/0822; A61L 9/01; A61L 2209/11; A61L 2209/16; B60H 3/0021; B60H 3/0035; B60H 1/3222
USPC .................. 123/339.17, 339.18, 179.3, 179.4
See application file for complete search history.

(56) References Cited

U.S. PATENT DOCUMENTS

| 5,297,988 | A | * | 3/1994 | Nishino | ................... A61L 9/12 222/644 |
| 5,664,423 | A | * | 9/1997 | Akazawa | ............. B60H 3/0007 62/303 |
| 6,494,778 | B2 | * | 12/2002 | Kossak | ..................... A61L 9/03 222/416 |
| 9,657,976 | B2 | | 5/2017 | Pebley et al. | |
| 2010/0129263 | A1 | * | 5/2010 | Arakawa | ............. B60H 3/0035 422/105 |
| 2015/0320899 | A1 | * | 11/2015 | Soliz | ........................ A61L 9/14 62/77 |

FOREIGN PATENT DOCUMENTS

| DE | 10328747 A1 | 1/2005 |
| EP | 2095980 A2 | 9/2009 |
| EP | 2684719 A2 | 1/2014 |
| FR | 3047900 A1 | 8/2017 |
| JP | 2013203354 A | 10/2013 |
| JP | 2013203355 A | 10/2013 |
| JP | 2013203356 A | 10/2013 |
| JP | 2013203358 A | 10/2013 |
| WO | 0232707 A1 | 4/2002 |
| WO | 2010090141 A1 | 8/2010 |

* cited by examiner

*Primary Examiner* — Hai H Huynh
(74) *Attorney, Agent, or Firm* — Geoffrey Brumbaugh; McCoy Russell LLP

(57) ABSTRACT

Methods and systems are provided for improving the operation of a start/stop vehicle having an FEAD-driven AC compressor. During an engine idle-stop, fragrance is dispensed into a vehicle cabin via a fragrance dispensing device integrated with a vent of a vehicle AC unit. The dispensed fragrance masks must smells attributed to an evaporator when the engine is shut-down, thereby extending the duration of idle-stop.

20 Claims, 4 Drawing Sheets

METHOD AND SYSTEM FOR ENGINE START/STOP CONTROL

FIELD

The present description relates generally to methods and systems for controlling a vehicle engine configured with start/stop capabilities to extend a duration of engine idle stop.

BACKGROUND/SUMMARY

Vehicle air conditioning (AC) systems may include AC compressors that are not electrically powered. In particular, they may be powered by a front end accessory drive (FEAD) of an engine, and may be connected to the FRAD through a system of belts and pulleys. When operated, the AC compressor pressurizes refrigerant flowing there-through based on cabin climate control demands of a vehicle customer. This enables the compressor to meet the desired cabin temperature set by the vehicle customer.

One issue with FEAD driven compressors is that the compressor does not work when the engine is turned off. As a result, while an engine is shutdown, there may be a rise in refrigerant temperature and a resulting increase in AC evaporator temperature. For a given blower speed setting, the increased evaporator temperature can generate an unpleasant musty odor which transfers to the passenger cabin and results in a drop in cabin air quality.

Various approaches have been developed to improve cabin air quality. One example approach is shown by Matsui et al. in JP2013203354. Therein, during an engine idle-stop, wherein an engine is shutdown responsive to a drop in torque demand, an AC system is moved to a fan only mode (from a heating or cooling mode) and a fragrance is delivered into a vehicle interior vehicle a fragrance delivery unit as a function of cabin air temperature. In particular, fragrance delivery is increased when cabin air temperature increases.

However, the inventors herein have recognized potential issues with such systems. As one example, the approach may cause a drop in the fuel savings, reduction in exhaust emissions, and reduction in noise that are achieved through idle-stop operations. In particular, the duration of the engine idle-stop may be limited by an evaporator temperature limit. In order to avoid a significant increase in the evaporator temperature, and the resultant humidity that drives the musty air, the engine may have to be restart ahead of high temperatures being reached in order to ensure that the customer does not get the musty smell. As a result, the engine-off time is reduced, which limits the opportunity of fuel economy and emission savings.

In one example, the issues described above may be addressed by a method comprising: delaying an engine restart from idle-stop by dispensing a fragrance through an air vent into a vehicle cabin. In this way, an engine idle-stop may be prolonged.

As an example, during an engine idle-stop, a fragrance dispensing device integrated into a vehicle heating ventilation and air conditioning (HVAC) system may be operated to extend the duration of the idle-stop. For example, an output of the fragrance dispensing device may be adjusted as a function of an odor and/or air quality sensor coupled to the interior of the vehicle to measure the humidity/musty level that is reaching the passenger cabin. If the sensor measurement exceeds a calibratable threshold during the idle-stop, diffusion rate of the fragrance may be increased to freshen up the air quality at the vent. The diffusion rate may be adaptively adjusted to the number of the passengers in the vehicle (such as may be detected via occupancy sensors). Further still, the diffusion rate can be adjusted as a function of the predicted duration of idle-stop, ambient temperature, and ambient humidity.

In this way, a duration of vehicle idle-stop can be prolonged while providing an improved air quality in a vehicle cabin. By reducing the need to restart a vehicle engine to avoid a musty odor, benefits related to engine idle-stop operations, such as reduced fuel economy and exhaust emissions, are extended over a longer portion of a vehicle drive cycle.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
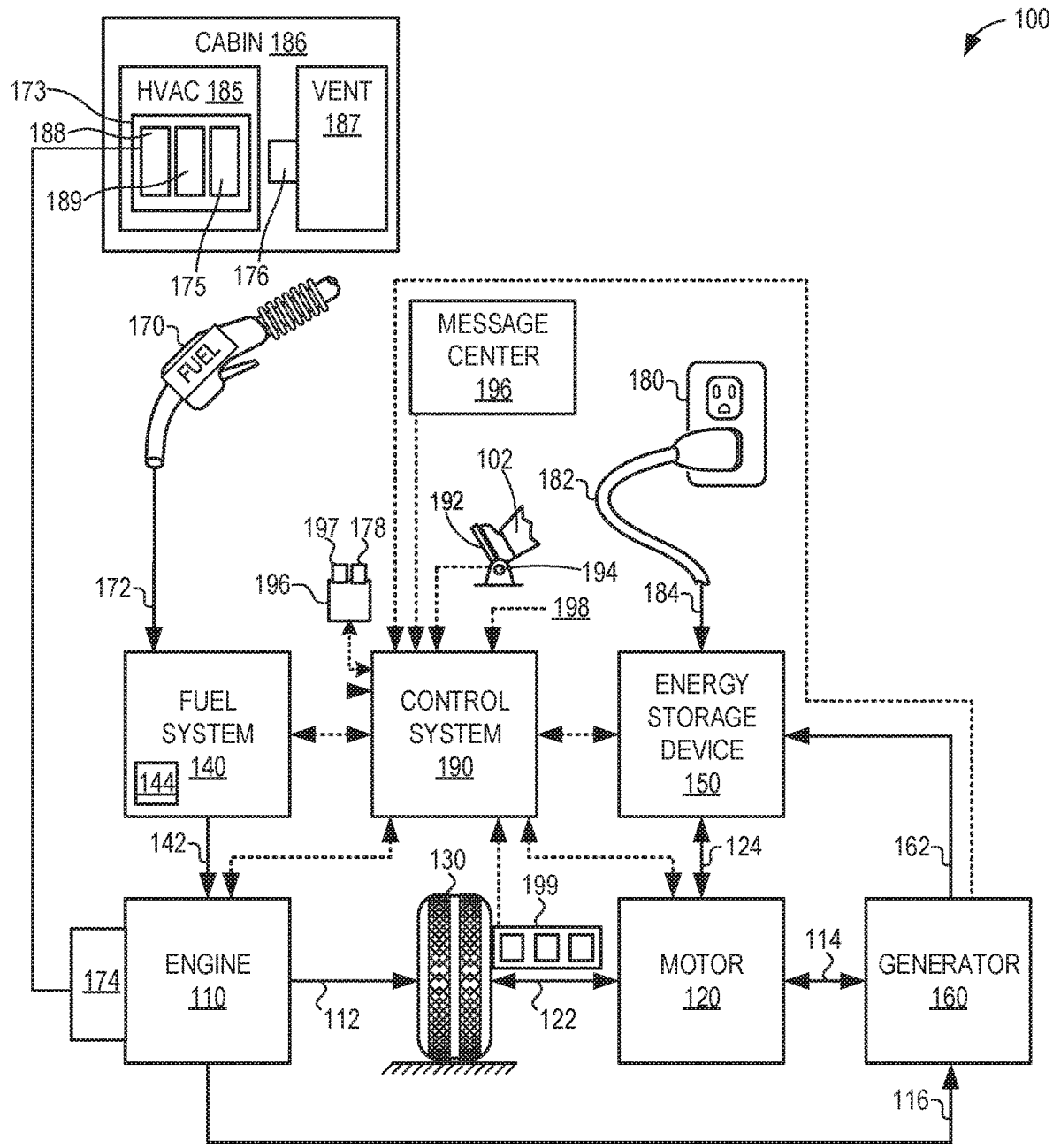
FIG. 1 shows an example vehicle system having a fragrance dispensing system integrated to the vehicle's ventilation system.
Figure 3:
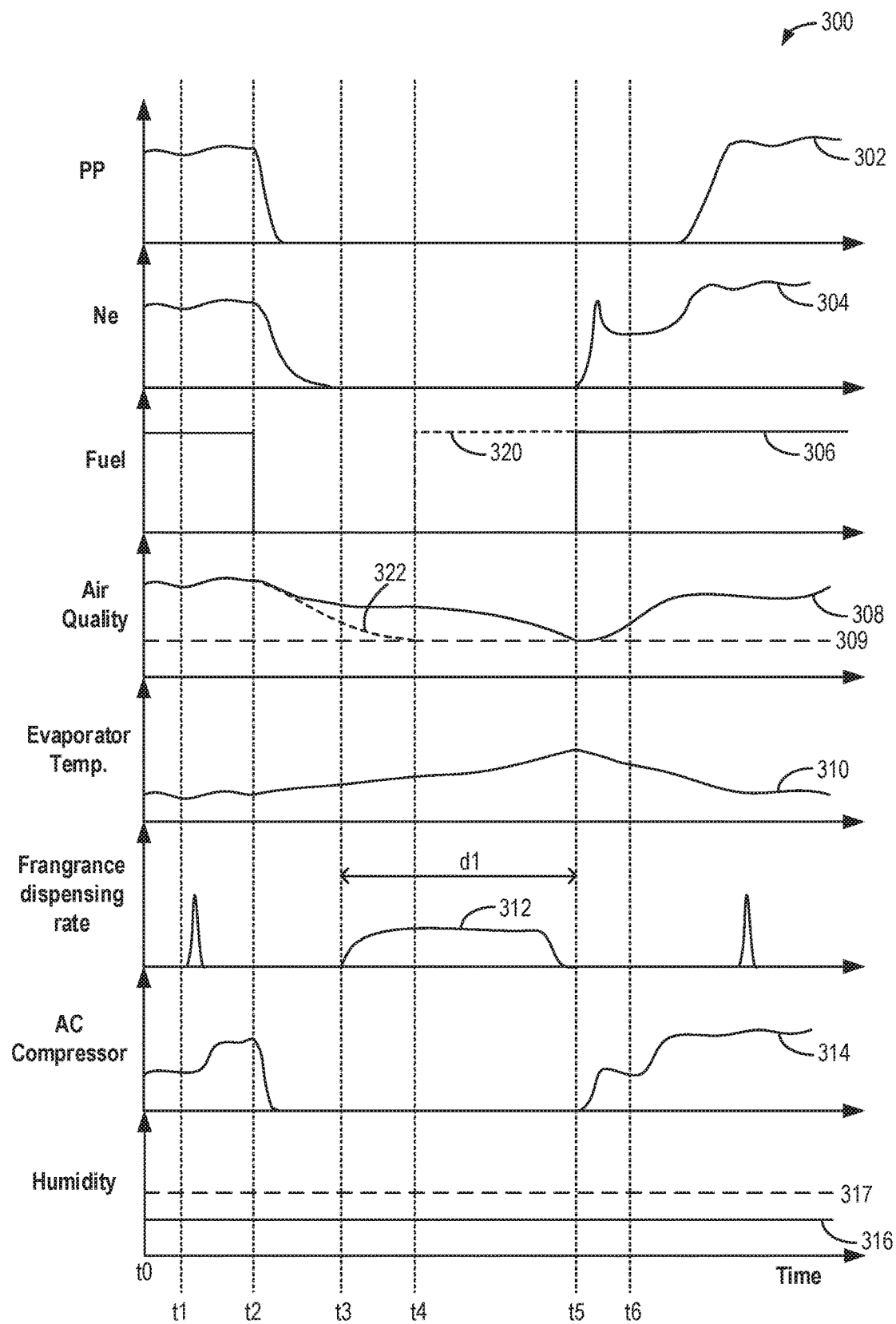
FIG. 3 shows a prophetic example of vehicle operation with cabin odor control during an idle-stop at lower ambient humidity.
Figure 4:
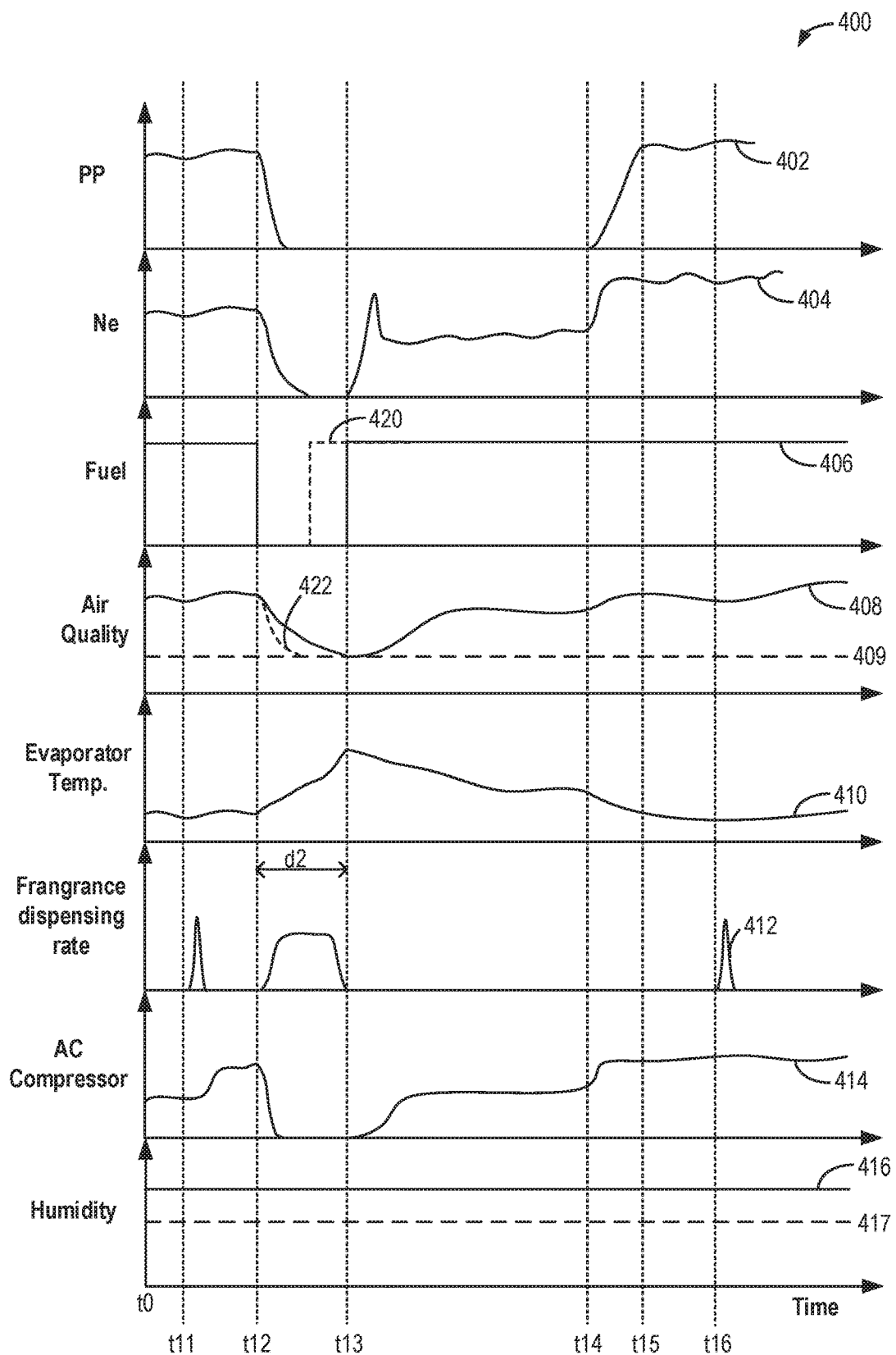
FIG. 4 shows a prophetic example of vehicle operation with cabin odor control during an idle-stop at higher ambient humidity.

The following description relates to systems and methods for extending a duration of engine idle-stop control in a vehicle system configured with a fragrance dispensing system integrated to vehicle ventilation operations. An example vehicle system is shown at FIG. 1. An engine controller may perform a control routine, such as the example routine of FIG. 2, to adjust a rate of fragrance dispensing during an engine idle-stop to reduce engine restarts due to musty cabin air. Example vehicle operations with changes to a rate and timing of fragrance dispersal during an engine idle-stop are shown at FIGS. 3-4.

FIG. 1 illustrates an example vehicle propulsion system 100. Vehicle propulsion system 100 includes a fuel burning engine 110 and a motor 120. As a non-limiting example, engine 110 comprises an internal combustion engine and motor 120 comprises an electric motor. Motor 120 may be configured to utilize or consume a different energy source than engine 110. For example, engine 110 may consume a liquid fuel (e.g., gasoline) to produce an engine output while motor 120 may consume electrical energy to produce a motor output. As such, a vehicle with propulsion system 100 may be referred to as a hybrid electric vehicle (HEV).

Vehicle propulsion system 100 may utilize a variety of different operational modes depending on operating conditions encountered by the vehicle propulsion system. Some of these modes may enable engine 110 to be maintained in an off state (i.e. set to a deactivated state) where combustion of fuel at the engine is discontinued. For example, under select operating conditions, motor 120 may propel the vehicle via drive wheel 130 as indicated by arrow 122 while engine 110 is deactivated.

During other operating conditions, engine 110 may be set to a deactivated state (as described above) while motor 120 may be operated to charge energy storage device 150. For example, motor 120 may receive wheel torque from drive wheel 130 as indicated by arrow 122 where the motor may convert the kinetic energy of the vehicle to electrical energy for storage at energy storage device 150 as indicated by arrow 124. This operation may be referred to as regenerative braking of the vehicle. Thus, motor 120 can provide a generator function in some embodiments. However, in other embodiments, generator 160 may instead receive wheel torque from drive wheel 130, where the generator may convert the kinetic energy of the vehicle to electrical energy for storage at energy storage device 150 as indicated by arrow 162.

During still other operating conditions, engine 110 may be operated by combusting fuel received from fuel system 140 as indicated by arrow 142. For example, engine 110 may be operated to propel the vehicle via drive wheel 130 as indicated by arrow 112 while motor 120 is deactivated. During other operating conditions, both engine 110 and motor 120 may each be operated to propel the vehicle via drive wheel 130 as indicated by arrows 112 and 122, respectively. A configuration where both the engine and the motor may selectively propel the vehicle may be referred to as a parallel type vehicle propulsion system. Note that in some embodiments, motor 120 may propel the vehicle via a first set of drive wheels and engine 110 may propel the vehicle via a second set of drive wheels.

In other embodiments, vehicle propulsion system 100 may be configured as a series type vehicle propulsion system, whereby the engine does not directly propel the drive wheels. Rather, engine 110 may be operated to power motor 120, which may in turn propel the vehicle via drive wheel 130 as indicated by arrow 122. For example, during select operating conditions, engine 110 may drive generator 160, which may in turn supply electrical energy to one or more of motor 120 as indicated by arrow 114 or energy storage device 150 as indicated by arrow 162. As another example, engine 110 may be operated to drive motor 120 which may in turn provide a generator function to convert the engine output to electrical energy, where the electrical energy may be stored at energy storage device 150 for later use by the motor.

Fuel system 140 may include one or more fuel storage tanks 144 for storing fuel on-board the vehicle. For example, fuel tank 144 may store one or more liquid fuels, including but not limited to: gasoline, diesel, and alcohol fuels. In some examples, the fuel may be stored on-board the vehicle as a blend of two or more different fuels. For example, fuel tank 144 may be configured to store a blend of gasoline and ethanol (e.g., E10, E85, etc.) or a blend of gasoline and methanol (e.g., M10, M85, etc.), whereby these fuels or fuel blends may be delivered to engine 110 as indicated by arrow 142. Still other suitable fuels or fuel blends may be supplied to engine 110, where they may be combusted at the engine to produce an engine output. The engine output may be utilized to propel the vehicle as indicated by arrow 112 or to recharge energy storage device 150 via motor 120 or generator 160.

In some embodiments, energy storage device 150 may be configured to store electrical energy that may be supplied to other electrical loads residing on-board the vehicle (other than the motor), including cabin heating and air conditioning, engine starting, headlights, cabin audio and video systems, etc. As a non-limiting example, energy storage device 150 may include one or more batteries and/or capacitors.

Control system 190 may communicate with one or more of engine 110, motor 120, fuel system 140, energy storage device 150, and generator 160. Control system 190 may receive sensory feedback information from one or more of engine 110, motor 120, fuel system 140, energy storage device 150, and generator 160. Further, control system 190 may send control signals to one or more of engine 110, motor 120, fuel system 140, energy storage device 150, and generator 160 responsive to this sensory feedback. Control system 190 may receive an indication of an operator requested output of the vehicle propulsion system from a vehicle operator 102. For example, control system 190 may receive sensory feedback from pedal position sensor 194 which communicates with pedal 192. Pedal 192 may refer schematically to a brake pedal and/or an accelerator pedal.

Energy storage device 150 may periodically receive electrical energy from a power source 180 residing external to the vehicle (e.g., not part of the vehicle) as indicated by arrow 184. As a non-limiting example, vehicle propulsion system 100 may be configured as a plug-in hybrid electric vehicle (HEV), whereby electrical energy may be supplied to energy storage device 150 from power source 180 via an electrical energy transmission cable 182. During a recharging operation of energy storage device 150 from power source 180, electrical transmission cable 182 may electrically couple energy storage device 150 and power source 180. While the vehicle propulsion system is operated to propel the vehicle, electrical transmission cable 182 may disconnected between power source 180 and energy storage device 150. Control system 190 may identify and/or control the amount of electrical energy stored at the energy storage device, which may be referred to as the state of charge (SOC).

In other embodiments, electrical transmission cable 182 may be omitted, where electrical energy may be received wirelessly at energy storage device 150 from power source 180. For example, energy storage device 150 may receive electrical energy from power source 180 via one or more of electromagnetic induction, radio waves, and electromagnetic resonance. As such, it should be appreciated that any suitable approach may be used for recharging energy storage device 150 from a power source that does not comprise part of the vehicle, such as from solar or wind energy. In this way, motor 120 may propel the vehicle by utilizing an energy source other than the fuel utilized by engine 110.

Fuel system 140 may periodically receive fuel from a fuel source residing external to the vehicle. As a non-limiting example, vehicle propulsion system 100 may be refueled by receiving fuel via a fuel dispensing device 170 as indicated by arrow 172. In some embodiments, fuel tank 144 may be configured to store the fuel received from fuel dispensing device 170 until it is supplied to engine 110 for combustion. In some embodiments, control system 190 may receive an indication of the level of fuel stored at fuel tank 144 via a fuel level sensor. The level of fuel stored at fuel tank 144 (e.g., as identified by the fuel level sensor) may be communicated to the vehicle operator, for example, via a fuel gauge or indication in a vehicle instrument panel 196.

The vehicle propulsion system 100 may also include an ambient temperature/humidity sensor 198, and a roll stability control sensor, such as a lateral and/or longitudinal and/or yaw rate sensor(s) 199. The vehicle instrument panel 196 may include indicator light(s) and/or a text-based display in which messages are displayed to an operator. The vehicle instrument panel 196 may also include various input portions for receiving an operator input, such as buttons, touch screens, voice input/recognition, etc. For example, the vehicle instrument panel 196 may include a refueling button 197 which may be manually actuated or pressed by a vehicle operator to initiate refueling. For example, as described in more detail below, in response to the vehicle operator actuating refueling button 197, a fuel tank in the vehicle may be depressurized so that refueling may be performed.

In an alternative embodiment, the vehicle instrument panel 196 may communicate audio messages to the operator without display. Further, the sensor(s) 199 may include a vertical accelerometer to indicate road roughness. These devices may be connected to control system 190. In one example, the control system may adjust engine output and/or the wheel brakes to increase vehicle stability in response to sensor(s) 199.

Vehicle propulsion system 100 may also include a heating ventilation and air conditioning (HVAC) system 185. HVAC system 185 may be configured to provide a climate-controlled air flow to a cabin space 186 of the vehicle through vent 187. The HVAC system 185 may include an air conditioning (AC) unit 173 having an AC compressor 188 and an evaporator 189. The AC compressor 188 is responsible for circulating refrigerant through evaporator coils. In the present example, compressor 188 is a non-electric compressor coupled to a front end accessory drive (FEAD) 174 of engine 10 via one or more belts and pulleys. As a result, compressor 188 is operated via engine 10, and therefore the compressor 188 does not operate when the engine is shut down. A blower 175 of the AC unit 173 draws air, drawn from the atmosphere, across the evaporator 189 coils where heat is extracted from the flowing air, the extracted heat used to heat the circulating liquid refrigerant. The heated refrigerant is then circulated to a condenser of the AC unit where the refrigerant is cooled so that it can be circulated through the evaporator again. The blower 175 settings as well as the rate at which refrigerant is circulated by the AC compressor 188 is determined as a function of cabin climate control settings selected by a vehicle operator via cabin climate control buttons 178 on interface 196.

A fragrance dispensing system 176 may also be coupled to vent 187 for dispensing a scent into cabin 186. In one example, the fragrance dispensing system 176 may be integrated into the HVAC system 185, such as to a blower of the AC unit. In some examples, the fragrance dispensing system may include multiple fragrance dispensing devices coupled to different vents, such as a first device coupled to a first front vent (coupled to a front region of vehicle cabin 186) and a second device coupled to a second back vent (coupled to a back region of the vehicle cabin). The fragrance dispensing device 176 may include one or more components such as a tank for storing a scent in a liquid form (e.g., essential oil or cologne), a heater for heating the liquid when dispensing is required, a diffuser having a nozzle for dispensing the fragrance, and a fan for varying the rate at which the fragrance is diffused. Based on user input, a controller may adjust the fragrance dispensing device's fan setting to increase or decrease scent diffusion. For example, a blower fan speed may be increased or decreased. As another example, the amount of fragrance dispensed may be increased or decreased.

In some examples, the tank of the fragrance dispensing device 176 may be configured to store multiple fragrances and a fragrance that is diffused during device operation is selectable by a vehicle operator from the multiple fragrance options available. In further examples, the fragrance dispensing device may deliver different scents based on the target location, such as a first scent to a cabin front region (were a driver is located) and a second, different scent to a cabin rear region (where a passenger is located). Further still, fragrance delivery may be coordinated with the delivery of associated audible and visible content to a vehicle display or interface via a controller. For example, a controller may deliver pictures, images, text messages, and/or audio messages to vehicle interface 196 with content related to the scent being dispensed. For example, the displayed content may explain the types of scent being delivered. In still other examples, the type of fragrance that is selected may be based on driver settings and/or selections predefined by the driver.

Vehicle 100 may be a start/stop vehicle wherein engine 110 is configured to be selectively deactivated when idle-stop conditions are met, such as when the vehicle is stopped at a traffic light and torque demand is reduced. At that time, engine fueling may be disabled and the engine may spin to rest. Then, when restart conditions are met, such as when the operator tips in, engine fueling may be resumed and the engine may spin up. The idle-stop operations enable fuel savings, a reduction in vehicle emissions, as well as a reduction in engine noise, vibration, and harshness (NVH).

As described above, the AC compressor 188 is driven by FEAD 174 and therefore cannot be operated when the engine is shutdown or idle-stopped. In particular, in the case of an FEAD driven AC compressor, the AC compressor is functioning through powering out of the FEAD when the engine is running. The compressor then works on pressuring the refrigerant based on climate commands from customer settings to meet the desired cabin temperature. Once the engine is turned off, the compressor is not working which results in an increase in refrigerant temperature and higher resultant evaporator temperature. For a given blower speed setting, the unpleasant musty odor resulting from the elevated evaporator temperature can transfer into the passenger cabin space 186 and drive an undesirable climate air quality. For start/stop vehicles with a non-electric AC compressor, the duration of the idle-stop may be limited by an evaporator temperature limit. In order to avoid a higher than threshold increase of the evaporator temperature and the resultant humidity that drives the musty air, the engine may need to be restarted ahead of high temperatures being reached in order to ensure that the customer does not get the musty smell. This can reduce the engine-off time and the opportunity for fuel economy and emission savings.

Figure 2:
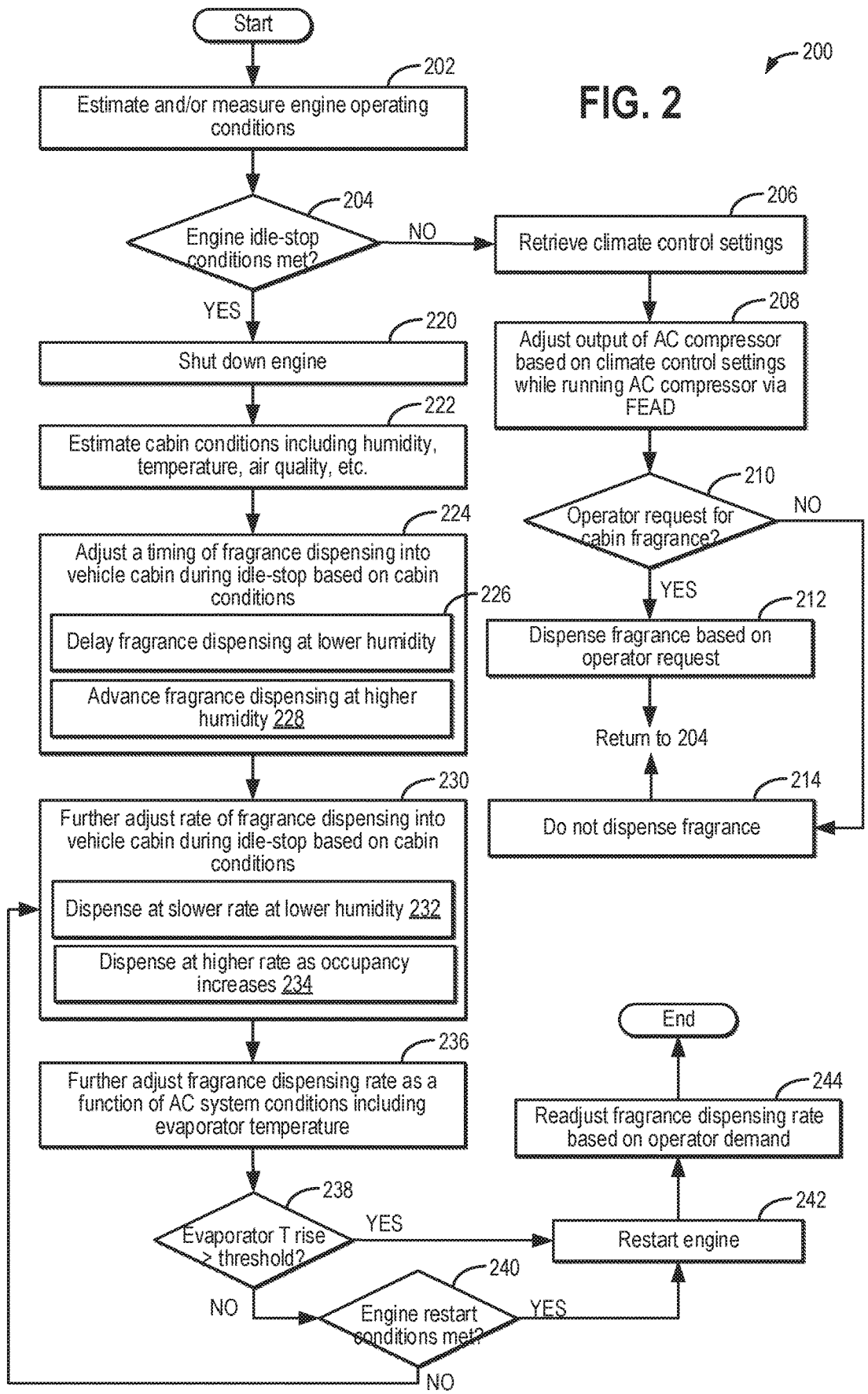
FIG. 2 shows a flow chart of an example method for extending a duration of engine idle-stopping via improvements to cabin air quality.

As elaborated herein with reference to FIG. 2, during an engine idle-stop, a controller may adjust fragrance release from the fragrance dispensing device 176 into cabin space 186 so as to maintain an improved cabin air quality. This allows a duration of idle-stop to be extended by delaying the need to restart the engine to avoid a musty smell in the cabin. By extending the duration of an idle-stop, fuel economy is improved. A controller may adjust a rate and timing of fragrance release as a function of cabin conditions, such as cabin humidity and temperature, as well as cabin occupancy level. Example adjustments in view of differences in humidity, and their impact on air quality, are shown with reference to FIGS. 3-4.

Control system 190 receives information from a plurality of sensors and sends control signals to a plurality of actuators. The plurality of sensors may include, for example, vehicle sensors 199, ambient humidity sensor 198, air quality sensors, refueling button 197, climate control button 178, etc. The plurality of actuators may include fuel injectors, blower 189, AC compressor 188, and fans coupled to fragrance releasing device 176. The control system 190 may include a controller that receives input data from the various sensors, processes the input data, and triggers the actuators in response to the processed input data based on instruction or code programmed therein corresponding to one or more routines. An example control routine is described herein with regard to FIG. 2. In this way, the controller receives signals from the various sensors and employs the various actuators to adjust engine operation based on the received signals and instructions stored on a memory of the controller. As an example, responsive to an operator request for cabin odor, the controller may operate the fan of the fragrance dispensing device to release a controlled amount of scent into the cabin space. In addition, during an engine idle stop, the controller may automatically adjust the fan setting for the fragrance dispensing device based on an estimated cabin air quality to extend a duration of engine idle-stop.

Turning now to FIG. 2, an example method 200 is shown for adjusting the operation of a fragrance dispensing device in a vehicle having a non-electric FEAD-driven AC compressor. By releasing a fragrance during an idle-stop to mask a musty cabin smell, a frequency of early engine restarts to improve cabin air quality is reduced. Instructions for carrying out method 200 may be executed by a controller based on instructions stored on a memory of the controller and in conjunction with signals received from sensors of the engine system, such as the sensors described above with reference to FIG. 1. The controller may employ engine actuators of the engine system to adjust engine operation, according to the methods described below.

At 202, the method includes estimating and/or measuring engine and vehicle operating conditions. These may include, for example, engine speed, torque demand, boost pressure, engine dilution, engine temperature, manifold pressure, vehicle speed, cabin climate control setting, ambient temperature, pressure, and humidity, cabin air quality, etc.

At 204, engine idle-stop conditions are assessed. Engine idle-stop conditions may be confirmed if, for example, the engine is operating (e.g., carrying out combustion), the state of charge (SOC) of a system battery is higher than a preset minimum threshold (e.g., above 30% SOC), the vehicle running speed is within a desired range (e.g., less than 30 mph), an air conditioning unit of the vehicle has not issued a request for operating a compressor, intake air temperature is within a target range, engine coolant temperature is above a threshold, and driver requested torque is less than a predetermined threshold. All engine idle-stop criteria need to be confirmed for an engine idle-stop to be confirmed. If any one of the criteria is not met, then an engine idle-stop is not confirmed. If engine idle-stop conditions are not confirmed, then the engine is maintained spinning with fuel being combusted in engine cylinders. The method then moves to 206.

At 206, while continuing to run the engine, cabin climate control settings for the vehicle may be retrieved. For example, climate control settings requested by a vehicle occupant may be retrieved via operator selection of climate control buttons on a vehicle interface (e.g., dashboard). The climate control settings may be include, for example, a desired cabin temperature and a desired blower or fan setting. At 208, the method includes adjusting the output of an AC compressor based on the operator selected climate control settings while running the AC compressor via an engine FEAD. Herein the AC compressor is a non-electric FEAD-driven compressor.

At 210, it is determined if a vehicle occupant has requested cabin fragrance. For example, a vehicle operator may request a fragrance to be dispensed into the vehicle cabin via actuation of a fragrance button on a vehicle dashboard. If yes, then at 212, the method includes dispensing fragrance into the cabin via actuation of a fragrance dispensing device integrated with the HVAC system of the vehicle. In one example, the controller may actuate a fan and/or heater of the fragrance dispensing device to dispense the fragrance. The amount of fragrance dispensed may be adjusted as a function of the climate control settings, such as based the settings of a blower of the AC unit. For example, as the amount of fragrance to be dispensed increases, a fan speed of the fragrance dispensing device may be increased. The method then returns to 204 to monitor engine idle-stop conditions. If the vehicle occupant has not requested cabin fragrance, then the method moves to 214 to not dispense fragrance, and then returns to 204 to resume monitoring idle-stop conditions.

At 204, if engine idle-stop conditions are confirmed (such as when all idle-strop criteria are met), the method moves to 220 to shut down the engine. This includes discontinuing fuel delivery to engine cylinders and spinning the engine down to rest. At 222, the method includes estimating cabin conditions while the engine is idle stopped. Cabin conditions estimated may include cabin temperature and humidity, as estimated via dedicated cabin sensors. Cabin conditions estimated may further include cabin air quality as inferred via an air quality or odor sensor coupled to the vehicle cabin.

At 224, the method includes automatically adjusting a timing of dispensing fragrance into the cabin based on cabin conditions estimated during the idle-stop. As such, due to the AC compressor being a non-electric compressor driven by the FEAD, when the engine is idle-stopped, the AC compressor also stops. This results in a gradual and eventual rise in temperature of the refrigerant stagnating in the evaporator, and a gradual increase in evaporator temperature. This, in turn, generates a musty smell which can permeate the cabin space and cause discomfort to the vehicle occupants. If the air quality degrades, the engine may have to be restarted earlier than otherwise intended to address the musty smell. However, by dispensing a fragrance via the fragrance dispensing device and adjusting the timing and rate of the diffusion based on cabin conditions during the idle-stop, the cabin air quality can be improved and the imminent engine restart can be delayed. Extending the duration of the engine idle-stop increases vehicle fuel economy and reduces exhaust emissions.

Adjusting the timing includes, at 226, delaying initiation of fragrance dispensing during the idle-stop when the ambient humidity is lower (e.g., lower than a non-zero threshold value). As another example, at 228, the method includes advancing initiation of fragrance dispensing during the idle-stop when the ambient humidity is higher (e.g., higher than the non-zero threshold value). As such, the cabin air quality and musty smell may be affected by cabin conditions such as ambient humidity. When the ambient humidity is elevated, the likelihood of a musty smell occurring during an idle-stop increases and even if the fragrance is dispensed, it may only have a limited impact. In other words, even with fragrance dispensing, the engine restart may be likely to occur soon. In such a scenario, the controller may limit fragrance usage, such as by providing a short burst of fragrance as soon as the engine is idle-stopped. The short bust may include an amount of scent dispensed over a short duration. In still other examples, the controller may not provide any fragrance when the ambient humidity is elevated and the engine restart is imminent.

In comparison, when the ambient humidity is lower, the likelihood of a musty smell occurring during an idle-stop decreases and the fragrance may have a larger impact when dispensed. In other words, with fragrance dispensing, the engine restart can be pushed further out and the idle-stop duration can be extended (assuming the engine is not restarted for other reasons such as operator torque demand). In such a scenario, the controller may try to extend fragrance usage, such as by starting to provide the fragrance after a duration has elapsed since the engine is idle-stopped. Further, the fragrance may be dispensed slowly and gradually, such as via an amount of scent dispensed over a long duration. Example operations are shown with reference to FIGS. 3-4. In still further examples, as the ambient humidity level increases, scent may be dispensed at a higher amount and/or rate to provide additional freshness.

It will be appreciated that while the example is described with reference to elevated cabin humidity, the timing of fragrance dispensing may be similarly adjusted as a function of cabin temperature. Therein fragrance may be dispensed earlier when ambient temperature is elevated and the musty smell is likely to occur earlier in the idle-stop, and fragrance may be dispensed later when ambient temperature is lower and the musty smell is likely to occur later in the idle-stop. Alternatively, at higher ambient temperatures, the controller may increase the amount and rate of fragrance dispensing to provide an additional anti-odor effect.

At 230, the method includes further adjusting a rate of fragrance dispensing into the vehicle cabin during the engine idle-stop based on cabin conditions. As an example, at 232, the fragrance is dispensed at a slower rate at lower humidity, and a higher rate at higher humidity. As another example, at 234, the fragrance is dispensed at a higher rate as cabin occupancy increases. As another example, an odor and/or air quality sensor can be utilized within the interior of the vehicle to measure the humidity/musty level that is reaching the passenger cabin. If the sensor measurement exceeds a calibratable threshold during the engine idle-stop, the controller may command an increase in the diffusion rate of the fragrance to freshen up the air quality at the vent.

The diffusion rate may be adapted to the number of the passengers in the vehicle, as detected via occupancy sensors, occupant weight detection sensors, and/or seat belt sensors. For example, if input from the occupancy sensor indicates that only the driver seat is occupied, then the controller may adjust the climate control vents to direct the fragrance towards the driver and reduce the fragrance diffusion amount and rate to a minimum level. As another example, if a passenger is included in addition to a vehicle driver, then the fragrance diffusion amount and rate may be increased.

For further accommodations of additional passengers in the vehicle, front and rear vents of the vehicle AC unit may include individualized fragrance dispensing units so that fragrance can be selectively delivered towards specific regions of the vehicle cabin. For example, a rear fragrance delivery unit coupled to a rear vent can be selectively operated responsive to input from a rear seat occupation sensor and/or responsive to a rear seatbelt being fastened.

In some examples, the fragrance delivery system may be configured to store multiple fragrances and the operator may select a fragrance from the multiple options to be delivered. Further, different scents may delivered based on the target location, such as a first scent to a cabin front region (were a driver is located) and a second, different scent to a cabin rear region (where a passenger is located). Further, pictures, images, text messages, and/or audio messages may be provided via a vehicle interface with content related to the scent being dispensed. For example, the displayed content may explain the types of scent being delivered, or may be based on a related theme. In still other examples, the type of fragrance that is select may be automatically selected based on driver settings and/or based on selections predefined by the driver via message settings, a switch, and/or audio settings.

Further still, the controller may adjust the dispensing of the fragrance as a function of a duration elapsed since the engine was shutdown. As the duration increases, the amount of fragrance dispensed may be increased. Alternatively, before the engine is shutdown, the controller may predict a duration of engine idle-stop based on navigational input including road grade, road conditions, weather conditions, and driver history. The controller may then adjust the rate of diffusion of the fragrance to last over the duration, or to further extend the duration.

In still further examples, the rate of dispensing may be adjusted as a function of fragrance availability, such as inferred from a fill level of a tank of the fragrance dispensing device. For example, as the fill level drops, the rate may be decreased.

In some examples, the controller may also disable dispensing of the fragrance responsive to opening of one of the plurality of windows. For example, if a vehicle window is opened by an operator, the cabin musty smell may be reduced and the cabin air quality may be improved via the admission of fresh ambient air into the cabin space. Accordingly, if any of the vehicle windows are opened, the controller may disable fragrance dispensing. Alternatively, the rate of fragrance dispensing may be reduced.

At 236 the controller may further adjust the rate of scent dispensing as a function of AC system conditions, such as evaporator temperature. Since the increase in evaporator temperature contributes to the musty smell in the vehicle cabin, the controller may monitor the absolute temperature of the evaporator relative to a temperature threshold (above which the engine needs to be restarted) as well as a rate of rise in evaporator temperature relative to a rate threshold (above which the engine needs to be restarted). As discussed earlier, the rate of rise in evaporator temperature over an idle-stop may be affected by ambient temperature and humidity. At 238, if the estimated rate of temperature rise at the evaporator is higher than the threshold rate, or if the evaporator temperature is higher than the threshold temperature, then at 242, the method includes restarting the engine. Herein the engine is restarted even though an increase in engine torque is not demanded by the operator. That is, the idle-stop condition is exited due to rise in evaporator temperature and the resulting drop in air quality. Restarting the engine includes resuming delivery of fuel to the engine and resuming fuel combustion in engine cylinders.

In still further examples, when the engine is auto-stopped in the idle-stop condition, if the customer requests "anti-odor and/or fragrance" to overcome a musty smell, instead of automatically restarting the engine, the controller may automatically adjust the user setting via a hardware switch and/or menu driven, to increase the amount of "anti-odor and/or fragrance" that is dispensed. Additionally or optionally, the controller may increase the blower fan speed. In still other examples, based on feedback from a sensor, one or more automatically controlled modules of the controller may automatically set the amount of anti-odor and/or fragrance and the fan speed to overcome the musty smell.

If the estimated rate of temperature rise at the evaporator is lower than the threshold rate, then at 240 the method includes confirming if engine restart conditions are otherwise met. In one example, engine restart conditions are met responsive to the engine being idle stopped, a torque requested by the driver being above a predetermined threshold, a request being made to operate an AC compressor to provide cabin heating or cooling, a battery state of charge being below a predetermined threshold (e.g., below 30% SOC), engine temperature (e.g., engine coolant temperature or catalyst temperature) being below a predetermined threshold, vehicle speed being greater than a threshold (e.g., above 3 mph), an accelerator pedal being depressed and/or a brake pedal being released, an engine electrical load being above a predetermined threshold, etc. Any one of the restart criteria may need to be met for restart conditions to be confirmed. If restart conditions are met, the method moves to 242 to restart the engine by resuming fuel delivery.

Irrespective of the reason due to which the engine is restarted, at 244, after restarting the engine, the method includes readjusting the fragrance delivery. For example, once the engine is restarted, it may be determined that odor control is not an issue anymore and fragrance delivery via the dispensing system is discontinued. As another example, fragrance delivery is returned to a default amount and level (and default scent) as selected by the operator in vehicle settings.

Example fragrance dispensing operations in a vehicle during an engine idle-stop are now shown with reference to FIGS. 3-4. Map 300 of FIG. 3 shows a first example where ambient humidity is lower than a threshold, and map 400 shows a second example where ambient humidity is higher than a threshold. Herein the vehicle is a start/stop vehicle.

Turning first to FIG. 3, map 300 depicts operator pedal position (PP, indicative of operator torque demand) at plot 302, and engine speed (Ne) at plot 304. Engine fueling (on or off) is depicted at plot 306. Air quality, as inferred from a sensor, is shown at plot 308. The air quality is compared to a threshold 309. AC evaporator temperature is shown at plot 310, and operation of an AC compressor is shown at plot 314. Ambient humidity is shown at plot 316 relative to a threshold 317. The operation of a fragrance dispensing device, including a dispensing rate, is shown at plot 312. All plots are depicted over time along the x-axis.

Between t0 and t2, the engine is operating fueled (plot 306) with fuel being combusted in engine cylinders to propel a vehicle. The vehicle is being driven in a region of lower than threshold 317 ambient humidity at this time (plot 316). The AC compressor is operated via a FEAD of the engine to provide an output that matches the operator's cabin cooling demand. Due to the AC compressor being operational, the AC evaporator temperature is low. The fragrance dispensing device is operated only when the operator requests scent, such as at t1. In response to the request, the controller may provide a short burst of a requested, or default scent (plot 312). Also between t0 and t2, the air quality is above threshold 309.

At t2, engine idle-stop conditions are met, such as due to drop in torque demand. Responsive to the idle-stop conditions being met, engine fueling is discontinued and the engine starts to spin to rest (plot 302). As a result of the engine being shutdown, the AC compressor also spins down, resulting in a gradual increase in evaporator temperature. The gradual increase in evaporator temperature results in a gradual drop in air quality, such as due to a musty smell coming into the cabin gradually from the evaporator.

Due to the lower than threshold ambient humidity, the drop in air quality is slower, and the impact of an air freshening action may be higher. To allow the engine idle stop that is initiated to be extended as far as possible while increasing the impact of fragrance dispensing, even though the idle-stop is initiated at t2, the fragrance dispensing device is not operated until t3. In other words, scent dispensing is delayed from t2 to t3, Further, due to the lower than threshold ambient humidity, fragrance is dispensed at a lower rate (than the burst provided at t1) and provided over a prolonged duration d1, from t3 to t5. Herein the fragrance dispensing between t3 and t5 is performed automatically, responsive to cabin conditions during the idle-stop, and without requiring explicit operator input requesting fragrance delivery. At t5, due to the air quality having dropped to threshold 309 even with the dispensing of the fragrance, the engine is restarted. As such, if the fragrance were not dispensed, the air quality would have dropped to the threshold at a faster rate, as indicated by dashed plot 322, and the engine would have been restarted by resuming fueling earlier, at t4, as indicated by dashed plot 320. Thus by dispensing the fragrance, the engine idle-stop is extended from t4 to t5, enabling additional fuel savings and emissions reductions benefits.

At t5, the engine is restarted by resuming fuel delivery. Herein the engine is restarted responsive to the drop in air quality requiring the engine to be restarted, and not due to an operator torque demand (which is received at t6). At t5, when the engine restarts, the AC compressor also starts to operate, the evaporator temperature starts to drop, and the cabin air quality starts to improve. At t6, an operator torque demand is received and engine output is accordingly adjusted to meet the torque demand. Thereafter the AC compressor operates based on cabin cooling demand. Also, the fragrance dispensing device operates responsive to operator input only, such as to provide a burst after t6.

Turning now to FIG. 4, map 400 depicts operator pedal position (PP, indicative of operator torque demand) at plot 402, and engine speed (Ne) at plot 404. Engine fueling (on or off) is depicted at plot 406. Air quality, as inferred from a sensor, is shown at plot 408. The air quality is compared to a threshold 309, which is the same as the threshold of FIG. 3. AC evaporator temperature is shown at plot 410, and operation of an AC compressor is shown at plot 414. Ambient humidity is shown at plot 316 relative to a threshold 317, which is the same as the threshold of FIG. 3. The operation of a fragrance dispensing device, including a dispensing rate, is shown at plot 412. All plots are depicted over time along the x-axis.

Between t0 and t12, the engine is operating fueled (plot 406) with fuel being combusted in engine cylinders to propel a vehicle. The vehicle is being driven in a region of higher than threshold 317 ambient humidity at this time (plot 416). The AC compressor is operated via a FEAD of the engine to provide an output that matches the operator's cabin cooling demand. Due to the AC compressor being operational, the AC evaporator temperature is low. The fragrance dispensing device is operated only when the operator requests scent, such as at t11. In response to the request, the controller may provide a short burst of a requested, or default scent (plot 412).

Also between t0 and t12, the air quality is above threshold 309.

At t12, engine idle-stop conditions are met, such as due to drop in torque demand. Responsive to the idle-stop conditions being met, engine fueling is discontinued and the engine starts to spin to rest (plot 402). As a result of the engine being shutdown, the AC compressor also spins down. Due to the higher than threshold ambient humidity, the shutting down of the compressor results in a faster rise in evaporator temperature (as compared to the example of FIG. 3 at lower ambient humidity). The faster increase in evaporator temperature results in a faster drop in air quality (as compared to the example of FIG. 3 at lower ambient humidity), such as due to a musty smell coming into the cabin gradually from the evaporator.

Due to the higher than threshold ambient humidity, the drop in air quality is faster, and the impact of an air freshening action may be smaller. To allow the engine idle stop that is initiated to be extended as far as possible while allowing the limited impact of fragrance dispensing to be provided, the fragrance dispensing device is initiated as soon as the engine idle-stop is initiated at t12. In other words, scent dispensing is not delayed. Further, due to the higher than threshold ambient humidity, fragrance is dispensed at a higher rate, such as at or around the rate at which the burst is provided at t11. Further, the fragrance is dispensed for a shorter duration d2, from t12 to t13. Herein duration d2 of FIG. 4 is shorter than duration d1 of FIG. 3. Further, the fragrance dispensing rate in the example of FIG. 4 is larger than the fragrance dispensing rate in the example of FIG. 3.

At t13, due to the air quality having dropped to threshold 309 even with the dispensing of the fragrance, the engine is restarted. As such, if the fragrance were not dispensed, the air quality would have dropped to the threshold shortly earlier, as indicated by dashed plot 422, and the engine would have been restarted by resuming fueling earlier, shortly before t13, as indicated by dashed plot 420. Thus by dispensing the fragrance, the engine idle-stop is extended, but only by a smaller amount. By limiting the fragrance dispensing during conditions, such as of high ambient humidity, when the impact of the fragrance is limited, the fragrance can be saved for a later idle-stop operation where it may have a more significant impact on extending the idle-stop duration.

At t13, the engine is restarted by resuming fuel delivery. Herein the engine is restarted responsive to the drop in air quality requiring the engine to be restarted, and not due to an operator torque demand (which is received at t14). At t13, when the engine restarts, the AC compressor also starts to operate, the evaporator temperature starts to drop, and the cabin air quality starts to improve. At t14, an operator torque demand is received and engine output is accordingly adjusted to meet the torque demand. Thereafter the AC compressor operates based on cabin cooling demand. Also, the fragrance dispensing device operates responsive to operator input only, such as to provide a burst at t16. In this way, fragrance is dispensed during an engine idle-stop at a lower rate and over a longer duration when the impact of the fragrance can be leveraged to extend the idle-stop. In comparison, fragrance dispensing is limited during an engine idle-stop when the impact of the fragrance cannot extend the idle-stop significantly.

In this way, fragrance can be dispensed adaptively and recursively from an existing fragrance dispensing device of a vehicle to extend a duration of an engine idle-stop. The technical effect of dispensing fragrance during a vehicle idle-stop in a vehicle having a non-electric, engine-driven AC compressor is that a drop in air quality due to a rise in evaporator temperature can be masked. By masking the musty smell from the evaporator, the need to restart an engine prematurely from an idle-stop, to improve the air quality in the cabin, is reduced. By extending a duration of engine idle-stops by reducing premature engine restarts, fuel savings are increased while exhaust emissions are decreased. In addition, customer satisfaction is improved.

One example vehicle method comprises delaying an engine restart from idle-stop by dispensing a fragrance through an air vent into a vehicle cabin during the idle-stop. In the preceding example, additionally or optionally, a rate and timing of the dispensing during the idle-stop is adjusted as a function of ambient humidity via a dispensing actuator coupled to a fragrance reservoir. In any or all of the preceding examples, additionally or optionally, when the ambient humidity is higher than a threshold, the fragrance is dispensed at a higher rate with a shorter delay since engine fueling is disabled on the idle-stop; and when the ambient humidity is lower than the threshold, the fragrance is dispensed at a lower rate with a longer delay since engine fueling is disabled on the idle-stop. In any or all of the preceding examples, additionally or optionally, the dispensing is further based on a duration elapsed since engine fueling is disabled on the idle-stop, a rate of the dispensing increased as the duration increases. In any or all of the preceding examples, additionally or optionally, the fragrance is dispensed via a fragrance dispensing device integrated into an air conditioning system of the vehicle and wherein a rate of the dispensing is adjusted based on cabin air quality as inferred from one or more of a rate of rise in temperature of an air conditioning system evaporator, and a cabin air quality sensor. In any or all of the preceding examples, additionally or optionally, the air conditioning system includes a compressor that is driven by a front end accessory drive (FEAD) of the engine. In any or all of the preceding examples, additionally or optionally, the method further comprises sensing vehicle occupancy including a number and location of occupants in the vehicle, and wherein the dispensing is further based on the sensed vehicle cabin occupancy.

Another example method for a vehicle comprises: operating a compressor of a vehicle air conditioning unit via an engine combusting fuel; responsive to a first engine idle-stop at higher ambient humidity, dispensing fragrance into a vehicle cabin at a first time since disabling fuel to the engine, and for a first duration; and responsive to a second engine idle-stop at lower ambient humidity, dispensing fragrance into the vehicle cabin at a second time since disabling fuel to the engine, and for a second duration, the second time later than the first time, the second duration longer than the first duration. In any or all of the preceding examples, additionally or optionally, the method further comprises disabling the compressor responsive to the disabling of fuel to the engine. In any or all of the preceding examples, additionally or optionally, fragrance is dispensed at a first rate during the first engine idle-stop and at a second rate, lower than the first rate, during the second engine idle-stop. In any or all of the preceding examples, additionally or optionally, the method further comprises monitoring a cabin air quality during both the first and second engine idle-stop, and restarting the engine responsive to monitored cabin air quality being lower than a threshold air quality. In any or all of the preceding examples, additionally or optionally, the engine is restarted after a first interval since disabling fuel at the first idle-stop and the engine is restarted after a second interval, longer than the first interval, since disabling fuel at the second idle-stop. In any or all of the preceding examples, additionally or optionally, the fragrance is dispensed into the vehicle cabin through a vent from a fragrance dispensing device having a fragrance reservoir, the device integrated with the vehicle air conditioning unit. In any or all of the preceding examples, additionally or optionally, a rate and direction of the dispensing during each of the first and second engine idle-stop is based on sensed vehicle occupancy.

Another example vehicle system comprises: a vehicle cabin space including an occupancy sensor for estimating cabin occupancy, and an air quality sensor for estimating cabin air quality; an engine; a front end accessory drive (FEAD) coupled to a crankshaft of the engine; an air conditioning (AC) unit including a vent coupled to the cabin space, a compressor driven by the engine via the FEAD, and an evaporator coupled to the compressor; a fragrance dispenser with a fragrance reservoir, the dispenser integrated with the AC unit and coupled to the cabin space via the vent; and a controller with computer-readable instructions stored on non-transitory memory that when executed cause the controller to: dispense fragrance into the vehicle cabin while the engine is combusting fuel responsive to operator request; and responsive to an engine idle-stop, disable engine fueling, and automatically dispense fragrance into the vehicle cabin space, one or more dispensing parameters adjusted as a function of input from each of the occupancy sensor and air quality sensor. In any or all of the preceding examples, additionally or optionally, the one or more dispensing parameters include a time of starting the dispensing, a duration of the dispensing, a rate of the dispensing, and a direction of the dispensing, wherein the rate and duration are increased as the cabin occupancy increase and/or the cabin air quality decreases. In any or all of the preceding examples, additionally or optionally, the cabin space further includes a humidity sensor for estimating ambient humidity, and a temperature sensor for estimating cabin temperature, and wherein a timing of the dispensing responsive to the engine idle-stop is adjusted as a function of one or more of the estimated ambient humidity and the estimated cabin temperature, the timing delayed as the humidity or the temperature decreases. In any or all of the preceding examples, additionally or optionally, automatically dispensing fragrance into the vehicle cabin responsive to an engine idle-stop includes dispensing the fragrance without receiving an operator request. In any or all of the preceding examples, additionally or optionally, the system further comprises a fragrance button coupled to a vehicle dashboard, and the controller includes further instructions that when executed dispense fragrance from the dispenser into the cabin space while the engine is running responsive to an operator request received via the fragrance button. In any or all of the preceding examples, additionally or optionally, the system further comprises a plurality of vehicle windows, and the controller includes further instructions that when executed disable dispensing of the fragrance responsive to opening of one of the plurality of windows.

In a further representation, the engine system is coupled in a hybrid electric vehicle. In a further representation, the engine system is coupled in an autonomous vehicle.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

As used herein, the term "approximately" is construed to mean plus or minus five percent of the range unless otherwise specified.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A vehicle method, comprising:
    delaying an engine restart from idle-stop by dispensing a fragrance through an air vent into a vehicle cabin during the idle-stop.

2. The method of claim 1, wherein a rate and timing of the dispensing during the idle-stop is adjusted as a function of ambient humidity via a dispensing actuator coupled to a fragrance reservoir.

3. The method of claim 2, wherein when the ambient humidity is higher than a threshold, the fragrance is dispensed at a higher rate with a shorter delay since engine fueling is disabled on the idle-stop; and when the ambient humidity is lower than the threshold, the fragrance is dispensed at a lower rate with a longer delay since engine fueling is disabled on the idle-stop.

4. The method of claim 3, wherein the dispensing is further based on a duration elapsed since engine fueling is disabled on the idle-stop, a rate of the dispensing increased as the duration increases.

5. The method of claim 1, wherein the fragrance is dispensed via a fragrance dispensing device integrated into an air conditioning system of the vehicle and wherein a rate of the dispensing is adjusted based on cabin air quality as inferred from one or more of a rate of rise in temperature of an air conditioning system evaporator, and a cabin air quality sensor.

6. The method of claim 5, wherein the air conditioning system includes a compressor that is driven by a front end accessory drive (FEAD) of the engine.

7. The method of claim 5, further comprising sensing vehicle occupancy including a number and location of occupants in the vehicle, and wherein the dispensing is further based on the sensed vehicle cabin occupancy.

8. A method for a vehicle, comprising:
operating a compressor of a vehicle air conditioning unit via an engine combusting fuel;
responsive to a first engine idle-stop at higher ambient humidity, dispensing fragrance into a vehicle cabin at a first time since disabling fuel to the engine, and for a first duration; and
responsive to a second engine idle-stop at lower ambient humidity, dispensing fragrance into the vehicle cabin at a second time since disabling fuel to the engine, and for a second duration, the second time later than the first time, the second duration longer than the first duration.

9. The method of claim 8, further comprising disabling the compressor responsive to the disabling of fuel to the engine.

10. The method of claim 8, wherein fragrance is dispensed at a first rate during the first engine idle-stop and at a second rate, lower than the first rate, during the second engine idle-stop.

11. The method of claim 8, further comprising, monitoring a cabin air quality during both the first and second engine idle-stop, and restarting the engine responsive to monitored cabin air quality being lower than a threshold air quality.

12. The method of claim 11, wherein the engine is restarted after a first interval since disabling fuel at the first idle-stop and the engine is restarted after a second interval, longer than the first interval, since disabling fuel at the second idle-stop.

13. The method of claim 8, wherein the fragrance is dispensed into the vehicle cabin through a vent from a fragrance dispensing device having a fragrance reservoir, the device integrated with the vehicle air conditioning unit.

14. The method of claim 8, wherein a rate and direction of the dispensing during each of the first and second engine idle-stop is based on sensed vehicle occupancy.

15. A vehicle system, comprising:
a vehicle cabin space including an occupancy sensor for estimating cabin occupancy, and
an air quality sensor for estimating cabin air quality;
an engine;
a front end accessory drive (FEAD) coupled to a crankshaft of the engine;
an air conditioning (AC) unit including a vent coupled to the cabin space, a compressor driven by the engine via the FEAD, and an evaporator coupled to the compressor;
a fragrance dispenser with a fragrance reservoir, the dispenser integrated with the AC unit and coupled to the cabin space via the vent; and
a controller with computer-readable instructions stored on non-transitory memory that when executed cause the controller to:
dispense fragrance into the vehicle cabin while the engine is combusting fuel responsive to operator request; and
responsive to an engine idle-stop, disable engine fueling, and automatically dispense fragrance into the vehicle cabin space, one or more dispensing parameters adjusted as a function of input from each of the occupancy sensor and air quality sensor.

16. The system of claim 15, wherein the one or more dispensing parameters include a time of starting the dispensing, a duration of the dispensing, a rate of the dispensing, and a direction of the dispensing, wherein the rate and duration are increased as the cabin occupancy increase and/or the cabin air quality decreases.

17. The system of claim 15, wherein the cabin space further includes a humidity sensor for estimating ambient humidity, and a temperature sensor for estimating cabin temperature, and wherein a timing of the dispensing responsive to the engine idle-stop is adjusted as a function of one or more of the estimated ambient humidity and the estimated cabin temperature, the timing delayed as the humidity or the temperature decreases.

18. The system of claim 15, wherein automatically dispensing fragrance into the vehicle cabin responsive to an engine idle-stop includes dispensing the fragrance without receiving an operator request.

19. The system of claim 15, further comprising a fragrance button coupled to a vehicle dashboard, wherein the controller includes further instructions that when executed:
dispense fragrance from the dispenser into the cabin space while the engine is running responsive to an operator request received via the fragrance button.

20. The system of claim 15, further comprising a plurality of vehicle windows, wherein the controller includes further instructions that when executed:
disable dispensing of the fragrance responsive to opening of one of the plurality of windows.

* * * * *